(12) United States Patent
Bischoff et al.

(10) Patent No.: US 10,849,692 B2
(45) Date of Patent: Dec. 1, 2020

(54) SYSTEM AND METHOD FOR INTRAOPERATIVE SURGICAL PLANNING

(71) Applicant: Zimmer, Inc., Warsaw, IN (US)

(72) Inventors: Jeffrey E. Bischoff, Warsaw, IN (US); Joanna Hucky, Kemptthal (CH)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 16/516,700

(22) Filed: Jul. 19, 2019

(65) Prior Publication Data

US 2019/0336223 A1 Nov. 7, 2019

Related U.S. Application Data

(63) Continuation of application No. 15/625,260, filed on Jun. 16, 2017, now Pat. No. 10,390,887.

(Continued)

(51) Int. Cl.
*A61B 34/10* (2016.01)
*G16H 50/50* (2018.01)
(Continued)

(52) U.S. Cl.
CPC .............. *A61B 34/10* (2016.02); *A61B 34/25* (2016.02); *A61F 2/30942* (2013.01);
(Continued)

(58) Field of Classification Search
CPC ... A61B 34/10; A61B 34/25; A61B 2034/102; A61B 2034/105; A61B 2034/2048;
(Continued)

(56) References Cited

U.S. PATENT DOCUMENTS 8,070,820 B2 * 12/2011 Winslow ............... A61F 2/4059
623/19.13
8,182,541 B2 * 5/2012 Long .................. A61B 17/1642
623/19.14
(Continued)

FOREIGN PATENT DOCUMENTS

CN 109475385 A 3/2019
EP 0872222 A1 * 10/1998 ............... A61F 2/40
(Continued)

OTHER PUBLICATIONS

"U.S. Appl. No. 15/625,260, Non Final Office Action dated Dec. 28, 2018", 6 pgs.
(Continued)

*Primary Examiner* — Jerome Grant, II
(74) *Attorney, Agent, or Firm* — Schwegman Lundberg & Woessner, P.A.

(57) ABSTRACT

The subject matter includes systems, methods, and prosthetic devices for joint reconstruction surgery. A computer-assisted intraoperating planning method can include accessing a first medical image providing a first view of a joint within a surgical site as well as receiving selection of a first component of a modular prosthetic device implanted in the first bone of the joint. The method continues by displaying a graphical representation of the first component of the modular prosthetic device overlaid on the first medical image, and updating a graphical representation of the first component based on receiving positioning inputs representative of an implant location of the first component relative to landmarks on the first bone visible within the first medical image. The method concludes by presenting a selection interface enabling visualization of additional components of the modular prosthetic device virtually connected to the first component and overlaid on the first medical image.

20 Claims, 10 Drawing Sheets

Related U.S. Application Data

(60) Provisional application No. 62/351,564, filed on Jun. 17, 2016.

(51) Int. Cl.

| | | |
|---|---|---|
| *A61B 34/00* | (2016.01) | |
| *A61F 2/30* | (2006.01) | |
| *A61F 2/46* | (2006.01) | |
| *A61B 34/20* | (2016.01) | |
| *A61B 90/00* | (2016.01) | |
| *A61B 17/00* | (2006.01) | |
| *A61F 2/40* | (2006.01) | |

(52) U.S. Cl.
CPC .......... *A61F 2/4657* (2013.01); *G16H 50/50* (2018.01); *A61B 2017/00203* (2013.01); *A61B 2017/00207* (2013.01); *A61B 2017/00216* (2013.01); *A61B 2034/102* (2016.02); *A61B 2034/105* (2016.02); *A61B 2034/108* (2016.02); *A61B 2034/2048* (2016.02); *A61B 2034/252* (2016.02); *A61B 2034/254* (2016.02); *A61B 2034/256* (2016.02); *A61B 2090/061* (2016.02); *A61B 2090/067* (2016.02); *A61B 2090/363* (2016.02); *A61B 2090/365* (2016.02); *A61B 2090/3966* (2016.02); *A61F 2/40* (2013.01); *A61F 2/4014* (2013.01); *A61F 2/4059* (2013.01); *A61F 2002/3008* (2013.01); *A61F 2002/4022* (2013.01); *A61F 2002/4632* (2013.01); *A61F 2002/4633* (2013.01); *A61F 2002/4658* (2013.01)

(58) Field of Classification Search
CPC ........ A61B 2034/254; A61B 2090/061; A61B 2090/067; A61B 2090/3966; A61B 2017/00203; A61B 2017/00207; A61B 2017/00216; A61B 2034/108; A61B 2034/252; A61B 2034/256; A61B 2090/363; A61B 2090/365; G16H 50/50; A61F 2/30942; A61F 2/4657; A61F 2/40; A61F 2002/3008; A61F 2002/4632; A61F 2002/4633; A61F 2/4014; A61F 2/4059; A61F 2002/4022; A61F 2002/4658
USPC .......................................................... 382/128
See application file for complete search history.

(56) References Cited

U.S. PATENT DOCUMENTS

| | | | |
|---|---|---|---|
| 8,236,059 B2* | 8/2012 | Stone .................... | A61F 2/4014 623/19.14 |
| 10,390,887 B2 | 8/2019 | Bischoff et al. | |
| 2004/0152970 A1 | 8/2004 | Hunter et al. | |
| 2004/0171924 A1* | 9/2004 | Mire ...................... | A61B 34/20 600/407 |
| 2005/0245817 A1 | 11/2005 | Clayton et al. | |
| 2005/0246020 A1 | 11/2005 | Southworth | |
| 2006/0161052 A1* | 7/2006 | Colombet .............. | A61B 5/064 600/300 |
| 2009/0089081 A1 | 4/2009 | Haddad | |
| 2013/0211792 A1* | 8/2013 | Kang ..................... | G09B 23/30 703/1 |
| 2015/0105828 A1 | 4/2015 | Reckling et al. | |
| 2016/0038245 A1 | 2/2016 | Park | |
| 2016/0100909 A1 | 4/2016 | Wollowick et al. | |
| 2016/0128654 A1 | 5/2016 | Wollowick et al. | |
| 2016/0287337 A1 | 10/2016 | Aram et al. | |
| 2017/0007330 A1* | 1/2017 | Britton .................. | A61F 2/4657 |
| 2017/0071673 A1* | 3/2017 | Ferro .................... | A61B 5/1079 |
| 2017/0178324 A1 | 6/2017 | Saget et al. | |
| 2017/0258526 A1* | 9/2017 | Lang ..................... | A61F 2/389 |
| 2017/0360510 A1* | 12/2017 | Bischoff ................ | A61B 34/10 |
| 2018/0256258 A1* | 9/2018 | Nash ...................... | A61B 34/20 |
| 2019/0365391 A1* | 12/2019 | Nikou ................ | A61B 17/1626 |
| 2020/0000527 A1* | 1/2020 | Cazal ........................ | G06T 7/74 |

FOREIGN PATENT DOCUMENTS

| | | | | |
|---|---|---|---|---|
| WO | WO-9522302 A1 * | 8/1995 | .......... | A61F 2/4059 |
| WO | WO-9522303 A1 | 8/1995 | | |
| WO | WO-9846172 A1 * | 10/1998 | .......... | A61F 2/4014 |
| WO | WO-2017218929 A1 | 12/2017 | | |

OTHER PUBLICATIONS

"U.S. Appl. No. 15/625,260, Notice of Allowance dated Apr. 10, 2019", 8 pgs.
"U.S. Appl. No. 15/625,260, Response filed Mar. 25, 2019 to Non Final Office Action dated Dec. 28, 2018", 11 pgs.
"Australian Application Serial No. 2017283631, First Examination Report dated Mar. 18, 2019", 3 pgs.
"Australian Application Serial No. 2017283631, Response Filed Mar. 29, 2019 First Examination Report dated Mar. 18, 2019", 22 pgs.
"International Application Serial No. PCT/US2017/037932, International Preliminary Report on Patentability dated Dec. 27, 2018", 9 pgs.
"International Application Serial No. PCT/US2017/037932, International Search Report dated Oct. 5, 2017", 6 pgs.
"International Application Serial No. PCT/US2017/037932, Written Opinion dated Oct. 5, 2017", 9 pgs.
U.S. Appl. No. 15/625,260, filed Jun. 16, 2017, System and Method for Intraoperative Surgical Planning.
"Australian Application Serial No. 2019216618, First Examination Report dated May 11, 2020", 4 pgs.
"Chinese Application Serial No. 201780045886.3, Office Action dated Oct. 18, 2019", (W/ English Translation), 8 pgs.
"Chinese Application Serial No. 201780045886.3, Response filed Feb. 17, 2020 Office Action dated Oct. 18, 2019", (W/ English Translation of Claims), 9 pgs.
"European Application Serial No. 17734205.2, Response filed Aug. 12, 2019 to Office Action dated Feb. 1, 2019", 39 pgs.
"Chinese Application Serial No. 201780045886.3, Office Action dated Jul. 17, 2020", with English translation, 5 pages.
"Chinese Application Serial No. 201780045886.3, Response filed Aug. 26, 2020 to Office Action dated Jul. 17, 2020", with English claims, 8 pages.

* cited by examiner

SYSTEM AND METHOD FOR INTRAOPERATIVE SURGICAL PLANNING

CLAIM OF PRIORITY

This application is a continuation of U.S. patent application Ser. No. 15/625,260, filed on Jun. 16, 2017, which claims the benefit of U.S. Provisional Patent Application Ser. No. 62/351,564, filed on Jun. 17, 2016, the benefit of priority of each of which is claimed hereby, and each of which is incorporated by reference herein in its entirety.

BACKGROUND

The shoulder joint is a complex joint with the scapula, clavicle and the humerus all coming together to enable a wide range of movement, at least in a properly functioning joint. In a properly functioning shoulder joint the head of the humerus fits into a shallow socket in the scapula, typically referred to as the glenoid. Articulation of the shoulder joint involves movement of the humeral head in the glenoid, with the structure of the mating surfaces and surrounding tissues providing a wide range of motion.

The complexity of the shoulder joint makes any traumatic damage to the joint particularly difficult to repair. Fractures can result in dislodged bone fragments and other challenging issues for the orthopedic surgeon to resolve, often with limited pre-operative planning.

OVERVIEW

The present inventors have recognized, among other things, that a problem to be solved can include providing trauma surgeons with tools that allow for accessible pre-operative and intraoperative planning for joint reconstruction operations. The background briefly introduces some challenges presented by traumatic injuries to the shoulder joint, which is used as the exemplary joint during the majority of the following discussion. The shoulder joint provides an excellent vehicle for describing the capabilities of the systems and methods discussed below. The systems and methods are described here principally for anatomical shoulder arthroplasty, however the systems and methods are similarly applicable to a reverse shoulder arthroplasty. Additionally, the systems and methods are similarly applicable to other joints of the body, such as wrist, knee, hip, or elbow joints. In particular, certain hip replacement systems utilize a compatible method implantation and would benefit from implementation of concepts discussed herein. Additionally, the type of intraoperative planning discussed below is new for joint reconstruction and/or replacement surgeries.

The concepts discussed here involve using medical images, such as X-ray, fluoroscope, computer-tomography (CT) among others, in conjunction with prosthesis systems that include various fiducial marks to enable pre-operative placement and intraoperative refinement. The systems and methods discussed below can also be used to assist in bone fragment placement intraoperatively.

In an example, the surgeon uses a handheld device, such as an iPad® from Apple Computer of Cupertino, Calif., to access the planning system. The surgeon accesses the planning application, accesses the patient's file, which brings up the main planning interface. The planning interface loads the images of the target joint. The images can include anterior-posterior (AP) views of the target joint and optionally a contralateral joint for comparison purposes. Comparison to the "normal" contralateral joint is helpful in determining correct placement and sizing of prosthesis, especially when the target joint is heavily damaged, as well as for bone fragment placement.

Once the patient images are loaded, the surgeon can begin pre-operatively planning by selecting the first component of a prosthesis system, and sizing the first component according to the provided images. In some examples, the surgeon can skip this pre-operative planning step, and proceed directly to implanting the first component. In the case of a shoulder reconstruction, the first component will be a distal stem of the modular shoulder prosthesis system. The systems and method discussed here use a multi-component prosthesis for reconstruction, but the methods are applicable to one-piece prosthetics as well.

Once the first component is implanted, the surgeon can continue use of the planning interface intraoperatively, by adjusting the virtual representation of the first component according to fiducial marks on the implanted first component. The virtual first component includes fiducial marks that correspond to those on the implanted first component, which provides a visual cue to the surgeon regarding how the actual implanted first component's position ended up relative to the anatomy.

Next, the surgeon can select and virtually position a second component of the modular prosthesis within the planning interface. Each additional component of the modular prosthesis has fiducial marks that are visible on the physical component and reproduced in the planning interface on the virtual representations to assist the surgeon in placement during implantation. The fiducial marks also enable refinement of the intraoperative plan through the planning interface as the surgery proceeds, by allowing the surgeon to update the virtual representations with how things are actually implanted.

After all the components of the modular prosthesis system are implanted, the surgeon can use the planning interface to assist with bone fragment placement. The planning interface can display multiple views of the target joint and the contralateral joint to assist in this portion of the procedure.

This overview is intended to provide an overview of subject matter of this document. The overview discusses the inventive subject matter in a general, non-limiting, manner to provide an introduction to the more detailed description provided below in reference to the various figures included in this disclosure. It is not intended to provide an exclusive or exhaustive explanation of the invention. The detailed description is included to provide further information about the present document.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

The headings provided herein are merely for convenience and do not necessarily affect the scope or meaning of the terms used.

DETAILED DESCRIPTION

Joint reconstruction and/or replacement procedures, such as shoulder arthroplasty (total or reverse), are complicated involved procedures where experience can make a significant difference in outcomes for a patient. While experience may provide insights into proper prosthesis selection and placement, the intraoperative planning systems and processes discussed here can provide even the most experienced surgeon with additional assistance in obtaining optimal outcomes.

Figure 1:
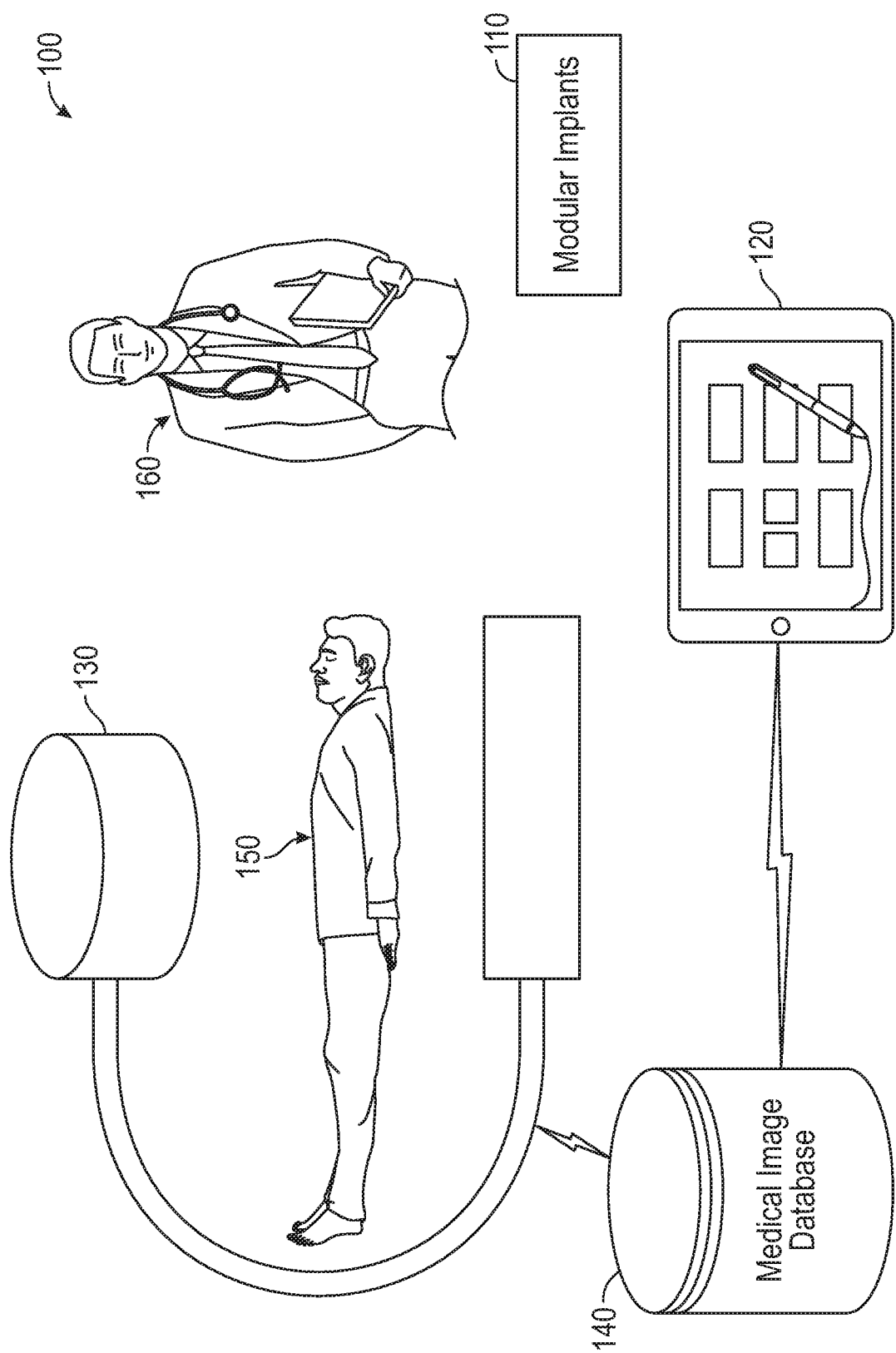
FIG. 1 is a block diagram illustrating an intraoperative planning system within a surgical environment, according to some example embodiments.

FIG. 1 is a block diagram illustrating an intraoperative planning system 120 within a surgical environment 100, according to some example embodiments. In this example, the surgical environment 100 includes a patient 150, a surgeon 160, a set of modular implants 110, an imaging device 130, an intraoperative planning system 120, and optionally a medical image database 140. In this example, the surgeon 160 (or other medical personnel) uses the imaging device 130 to obtain pre-operative medical images of a joint of the patient 150 targeted for repair or replacement. The imaging device 130 can be an x-ray to similar medical imaging device commonly used for imaging during (or prior to) arthroplasty procedures. The medical images can be transmitted to and retained by a medical image database 140, which can then be accessed by the intraoperative planning system 120. In another example, the medical image database 140 can be integrated within the intraoperative planning system 120, or the images can be sent directly to the intraoperative planning system 120 bypassing the medical image database 140.

Once preoperative imaging is complete the surgeon 160 can use the modular implants 110 and the intraoperative planning system 120 to perform the intended reconstruction or replacement surgery on patient 150. Discussion of FIGS. 2-6 below describes an example procedure in reference to a shoulder reconstruction or replacement using a modular shoulder prosthesis. The basic procedure and related concepts are applicable to reconstruction or replacement over other joints, such as wrist, elbow, hip, knee, or ankle joints.

Figure 2:
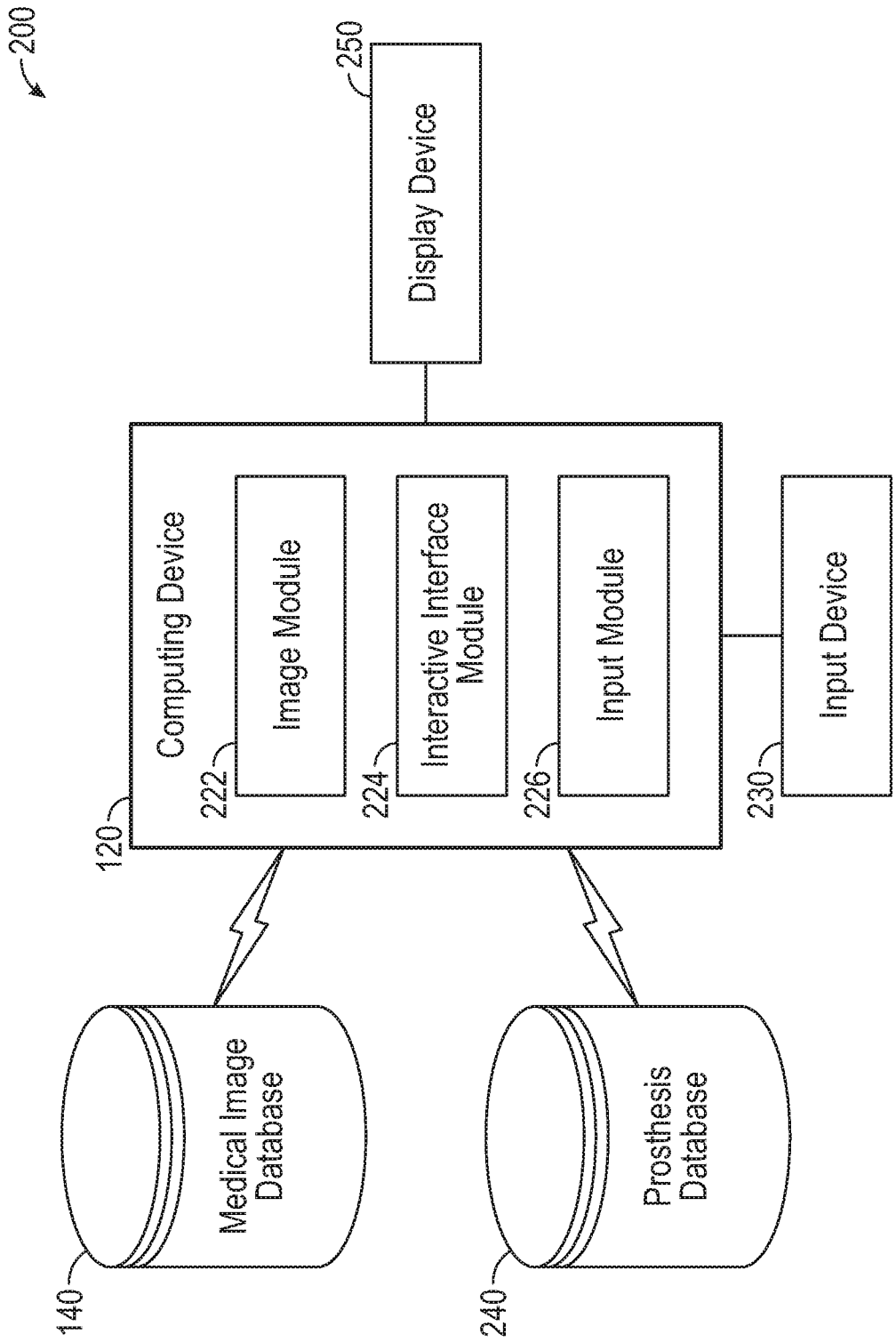
FIG. 2 is a block diagram illustrating an intraoperative planning system, according to some example embodiments.

FIG. 2 is a block diagram of an intraoperative planning system 200, according to some example embodiments. In this example, the intraoperative planning system 200 includes computing device 120, medical image database 140, input device 230, prosthesis database 240, and display device 250. In some examples, computing device 120 integrates some or all of the components, such as the medical image database 140, prosthesis database 240, input device 230, and display device 250. For example, the intraoperative planning processes and interfaces discussed here can operate as an application within an iPad® or similar handheld device. In an example, an iPad® can access external data, such as from the medical image database 140 and/or prosthesis database 240, over a network and integrates input device 230 and display device 250 into the main computing device 120. In another example, an iPad® can also host at least portions of the medical image database 140 and prosthesis database 240.

In this example, the computing device 120 includes an image module 222, an interactive interface module 224, and an input module 226. The image module 222 handles operations involving the medical images used in the intraoperative planning process, such as accessing and displaying the images. The image module 222 can scale the images as necessary to allow proper relationships between the virtual prosthesis and the medical images. The interactive interface module 224 handles operations supporting the planning process, such as display and manipulation of virtual prosthesis models within the planning interface. The input module 226 handles receiving user input to the computing device 120, such as receiving touch inputs manipulating position of a virtual representation of a portion of the modular prosthesis within the planning interface.

Figure 3:
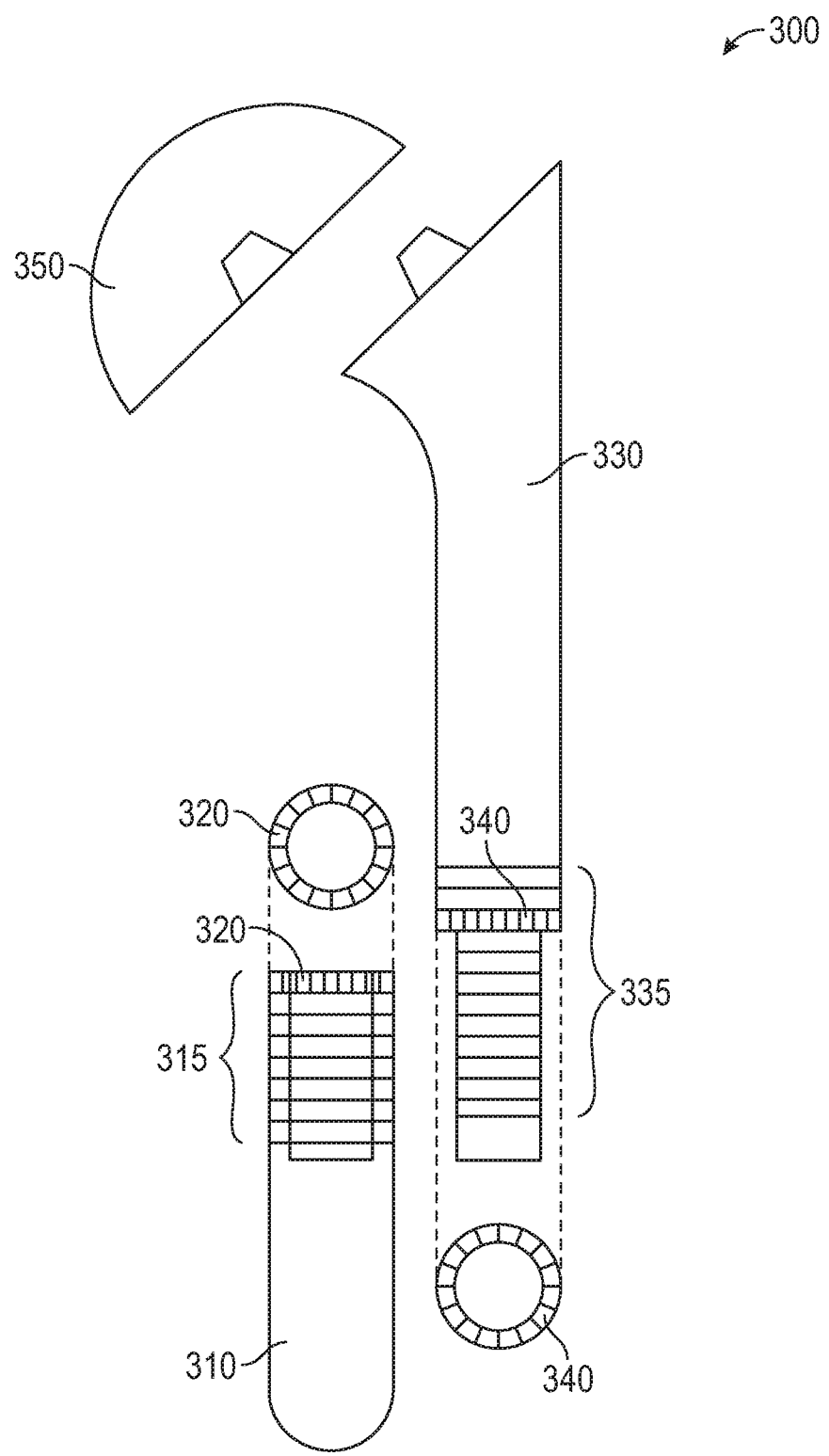
FIG. 3 is a diagram illustrating a modular shoulder prosthesis, according to some example embodiments.

FIG. 3 is a diagram illustrating a modular anatomical shoulder prosthesis 300, according to an example embodiment. In this example, the shoulder prosthesis 300 includes components such as a distal stem 310, a proximal stem 330 (as referred to as an adaptor 330), and a modular head 350. The distal stem 310 has fiducial marks for both height 315 and version (rotation) 320. The version fiducial marks 320 are illustrated as occurring around the circumference of a proximal portion of the distal stem 310, as well as projected onto the top cylindrical distal surface of the distal stem 310. The proximal stem or adaptor 330 also has fiducial marks for both height 335 and version (rotation) 340, which can be used intraoperatively to position the proximal stem 330 at the proper height and rotation relative to the distal stem 310. The proximal stem 330 has features to connect to additional modular components, including a modular humeral head 350.

Figure 4:
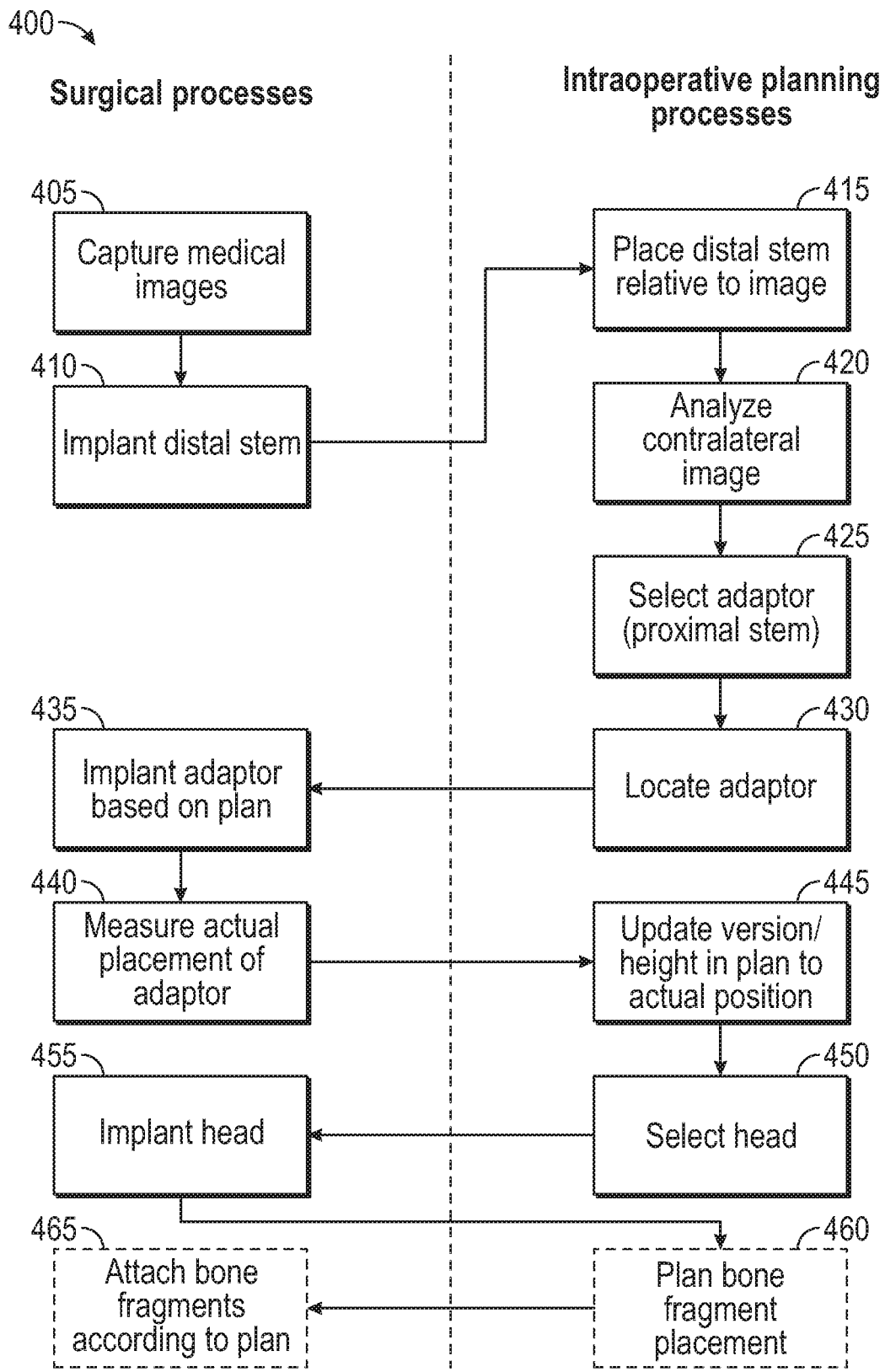
FIG. 4 is a flowchart illustrating interaction between surgical procedure and an interactive planning process, according to some example embodiments.

FIG. 4 is a flowchart illustrating a procedure 400 including illustration of interactions between surgical processes and interactive planning processes, according to some example embodiments. In this example, the procedure 400 includes operations such as: capturing medical images at 405, implanting a distal stem at 410, placing a virtual distal stem relative to an image at 415, analyzing contralateral image at 420, selecting a (virtual) adaptor at 425, locating the virtual adaptor at 430, implanting an adaptor at 435, measuring actual placement of adaptor at 440, updating version and height in plant to actual position at 445, selecting a head at 450, implanting the head at 455, optionally planning bone fragment placement at 460, and optionally attaching bone fragments at 465.

In this example, the procedure 400 begins at 405 with medical personnel capturing x-ray, or similar, images of the joint targeted for reconstruction and a contralateral joint. While capturing images of the contralateral joint is optional, the planning interface provides some additional benefits in terms of visualization, implant selection, and positioning when contralateral images are included. Even without contralateral images the planning interface can provide visualization, selection, and positioning benefits not otherwise readily available to surgeons in the operating room. The angle or view captured may depend upon the particulars of the target joint. For example, in shoulder reconstruction AP view of the target joint and the contralateral joint will be captured, and optionally axial and medial-lateral (ML) views may be captured. The planning interface can be configured to utilize any standard angles for views used in particular joint procedure.

At 410, the procedure 400 continues with the surgeon implanting the distal stem (first component of shoulder prosthesis). The surgeon implants the distal stem to an ideal depth based on conditions of the patient's anatomy. The planning process is specifically designed to adapt to conditions encountered during the surgery. At 415, the procedure 400 continues within the intraoperative planning system 200 with the surgeon (or support medical personnel) selecting and positioning a virtual representation of the distal stem relative to the medical image(s) displayed within the planning interface. For example, the intraoperative planning system 200 can display an AP view of the target joint and the contralateral joint and allow placement of a distal stem (first component of a modular prosthesis system) in reference to the images. The planning interface, which is described further below in reference to FIGS. 5A to 5F, also includes graphical representation of fiducials on the distal stem. The fiducial marks on the distal stem allow for greater visualization and quantification of position of the implant in the anatomy. Translating the physical fiducial marks into the virtual planning interface allows for the intraoperative planning to adjust to the actual reality of the surgical procedure.

At 420, the procedure 400 continues with the surgeon using the intraoperative planning system 200 to analyze the contralateral image, which can include determining or reviewing a target height and version for the implant from the contralateral image. In this example, the intraoperative planning system 200 displays, side-by-side, the AP and or axial views of the target joint and the contralateral joint. The surgeon can use the planning interface to experimentally position a portion of the prosthesis system to assist in determining a target height version for implantation of the first part of the prosthesis system.

At 425, the procedure 400 continues with the surgeon using the intraoperative planning system 200 to select an adaptor (proximal stem in the shoulder example). At 425 and 430, the intraoperative planning system 200 allows the surgeon to virtually try different sizes and positions for the next part of the modular prosthesis system, such as a proximal stem. The surgeon can, within the planning interface at operation 430, position and rotate the virtual proximal stem and visualize it against both the target joint and the contralateral joint, which still has intact anatomy.

At 435, the procedure 400 continues with the surgeon implanting the proximal stem according to the plan generated within the intraoperative planning system 200. In this example, the proximal stem includes fiducial marks to assist the surgeon in duplicating the version (rotation) and height (if adjustable) as planned within the intraoperative planning system 200. Once the proximal stem is implanted, the procedure 400 continues at 440 with the surgeon measuring the actual end position of the proximal stem. Measurements can be taken using the fiducial marks on the proximal stem (prosthesis component) in reference to boney landmarks or the distal stem. It some procedures the surgeon may alter the planned implant location based on experience or conditions encountered within the surgical site. Accordingly, measurements of the actual implant location are taken and used to adjust the planning process. In the shoulder example, the height and version (rotation) of the proximal stem can be determined after implantation and adjustment of the actual implant.

At 445, the procedure 400 continues with the surgeon or medical personnel update the plan within the intraoperative planning system 200 to reflect actual conditions within the patient. In some examples, the procedure 400 continues at 450 with selection of the head or third component of a modular prosthesis system. Again the intraoperative planning system 200 enables the surgeon to try different sizes and positioning to plan implantation of the head component. The intraoperative planning system 200 can pull from a database of available prosthesis components, such as prosthesis database 240. Finally, the procedure 400 can complete at 455 with the surgeon implanting the head according to the plan.

Optionally, at 460, the procedure 400 can include planning for bone fragment placement. In this optional example, the intraoperative planning system 200 includes an interface that enables the surgeon to identify, locate, collect, and relocate (e.g., position) bone fragments. In reconstructions stemming from traumatic injuries it is not uncommon for the orthopedic surgeon to need to locate and arrange bone fragments. Being able to perform this virtually can assist in accelerating this portion of the surgical procedure. Procedure 400 illustrates bone fragment planning being done intraoperatively near the end of the over all procedure, which may be generally preferable as the implant locations are known at this point in the procedure 400. However, the bone fragment planning could be done anytime after the images are loaded into the intraoperative planning system 200. At 465, the procedure 400 continues with the surgeon attaching bone fragments as planned.

Figure 5A:
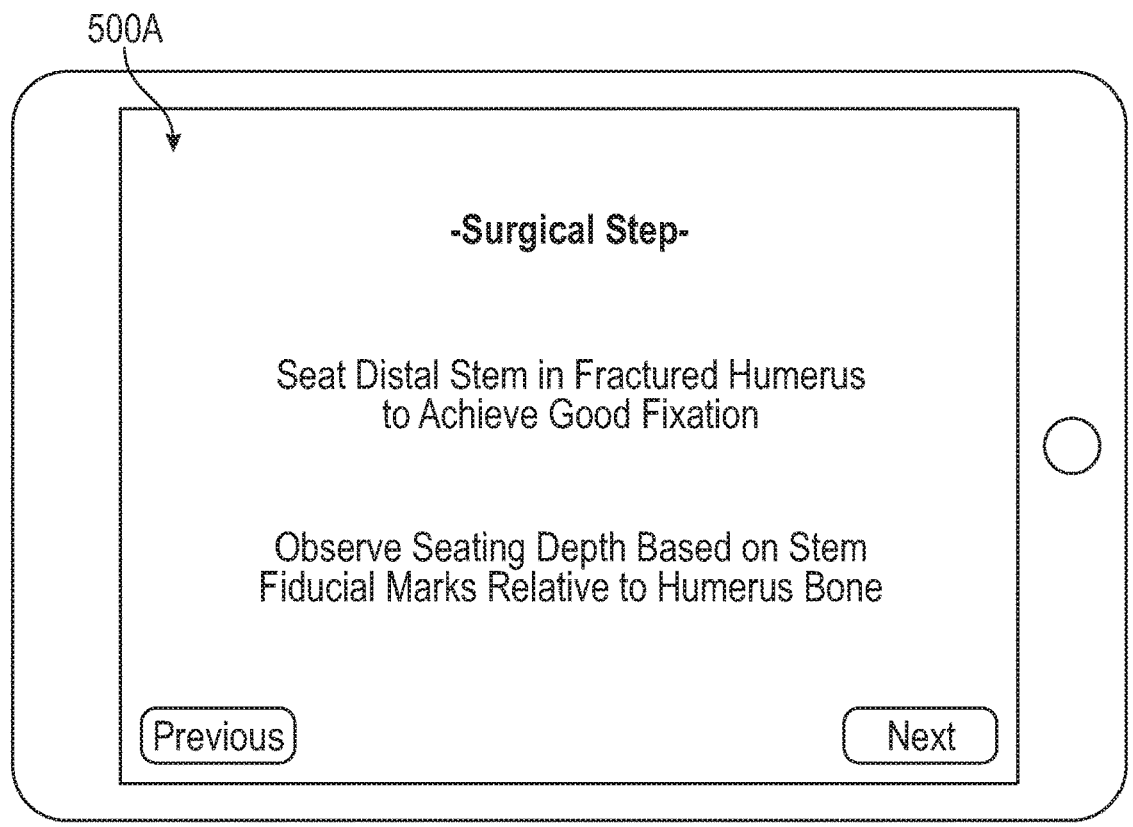
FIGS. 5A-5F are diagrams illustrating an intraoperative planning interface, according to some example embodiments.

FIGS. 5A-5F are diagrams illustrating an intraoperative planning interface, according to some example embodiments. These figures show some example interfaces that implement at least portions of the procedures discussed in FIG. 4 and FIG. 6. The interfaces shown can operate on an iPad® or similar handheld touchscreen device. FIG. 5A depicts an interface 500A with instructions for a surgical operation, in this example the surgical operation is implanting of the distal stem.

Figure 5B:
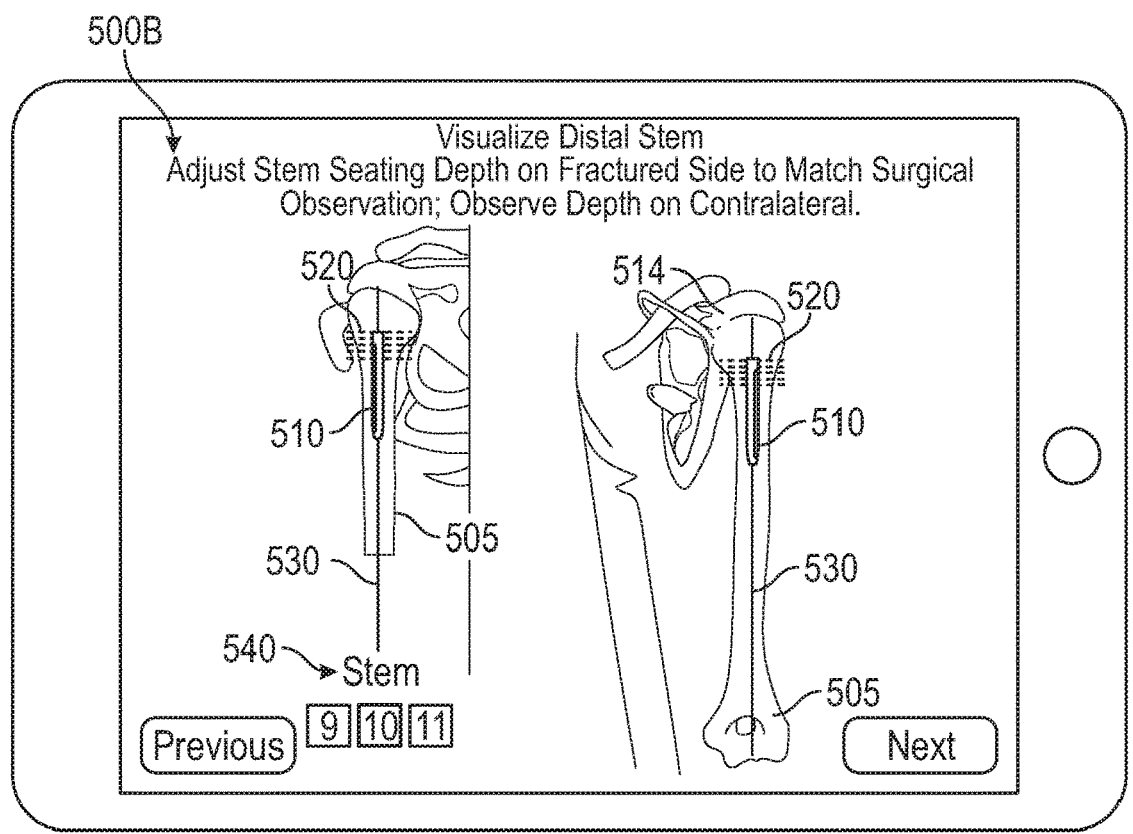

FIG. 5B depicts a component selection and positioning interface 500B. The interface 501 illustrates a humerus 505, a distal stem 510, virtual fiducial marks 520, a longitudinal axis (or anatomical axis) of the humerus 530, and a stem selection control 540. The virtual fiducial marks 520 correspond to physical fiducial marks on the distal stem implanted in the patient. The interface 500B provides visualization between the virtual distal stem and the implanted distal stem through graphical elements such as the virtual fiducial marks 520 and the longitudinal axis 530.

Figure 5C:
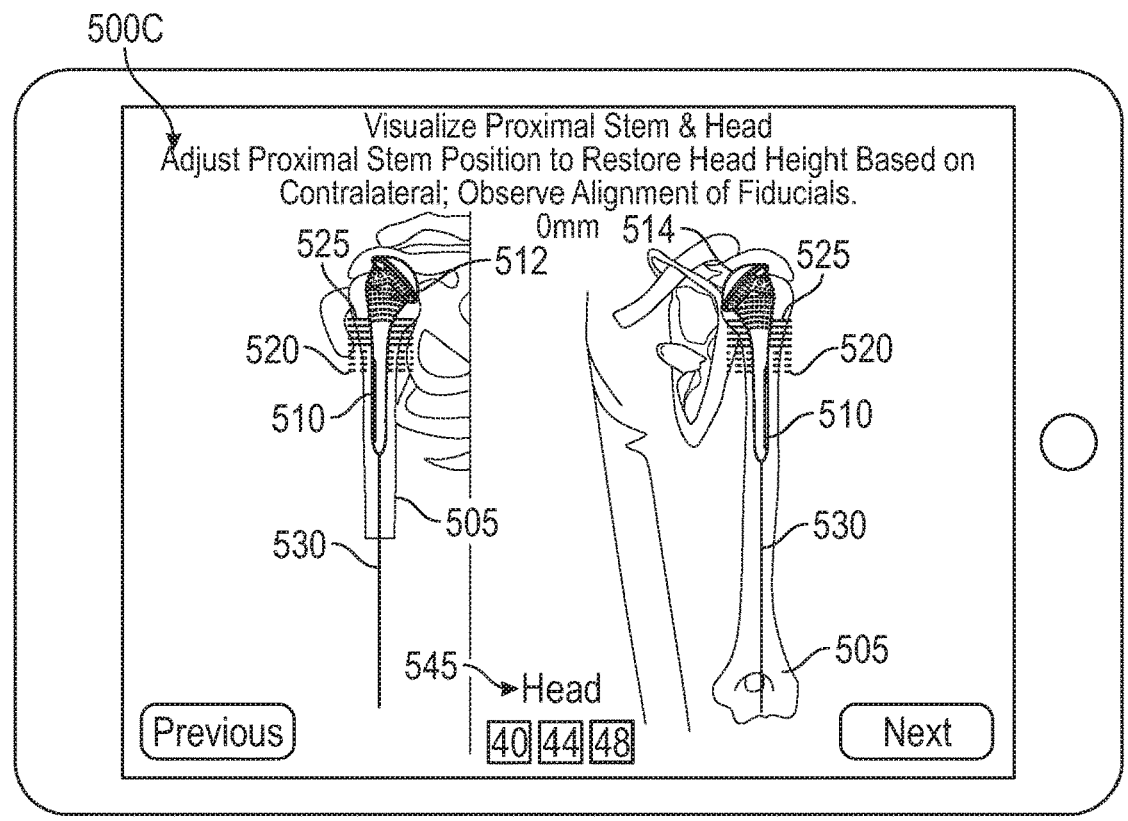
Figure 5D:
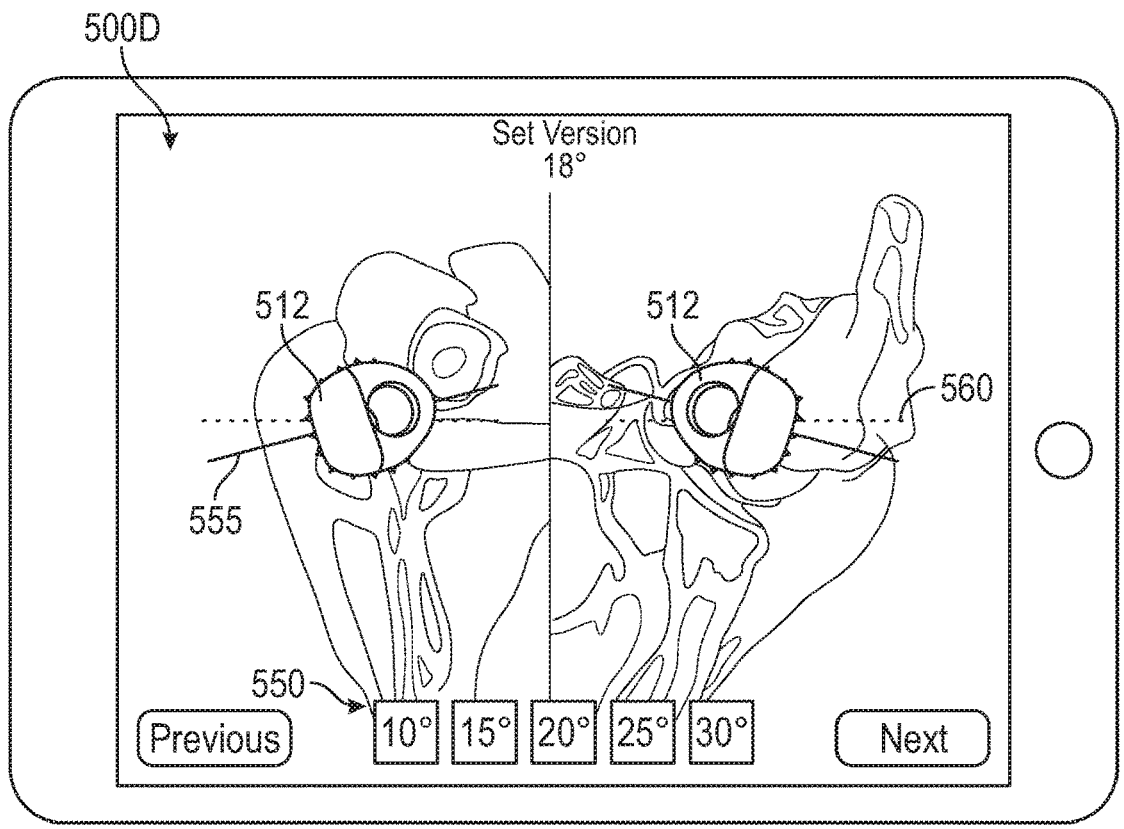

FIG. 5C depicts another planning interface 500C, which in this example includes the humerus 505, a distal stem 510, proximal stem 512, head 514, virtual fiducial marks on a distal stem 520, virtual fiducial marks on a proximal stem 525, a longitudinal axis (or anatomical axis) of the humerus 530, and head selection control 545. The second set of virtual fiducial marks 525 is associated with the proximal stem 512 in this example. The head selection control 545 enable selection of different size heads to evaluate best fit. FIG. 5D illustrates planning interface 500D, which in this example depicts a planning interface enabling a surgeon to adjust version of a proximal stem. In this example, the planning interface 500D includes axial images of the humerus 505 overlaid with proximal stem 512, version indicator 555, medial-lateral plane indicator 560, and version selection control 550. In some examples, the version selection control 550 provides for finer control, but is dependent upon the increments allowed by the physical prosthesis components. This interface, depicted in FIG. 5C for an anatomical reconstruction of the shoulder, is also applicable to a reverse shoulder reconstruction.

Figure 5E:
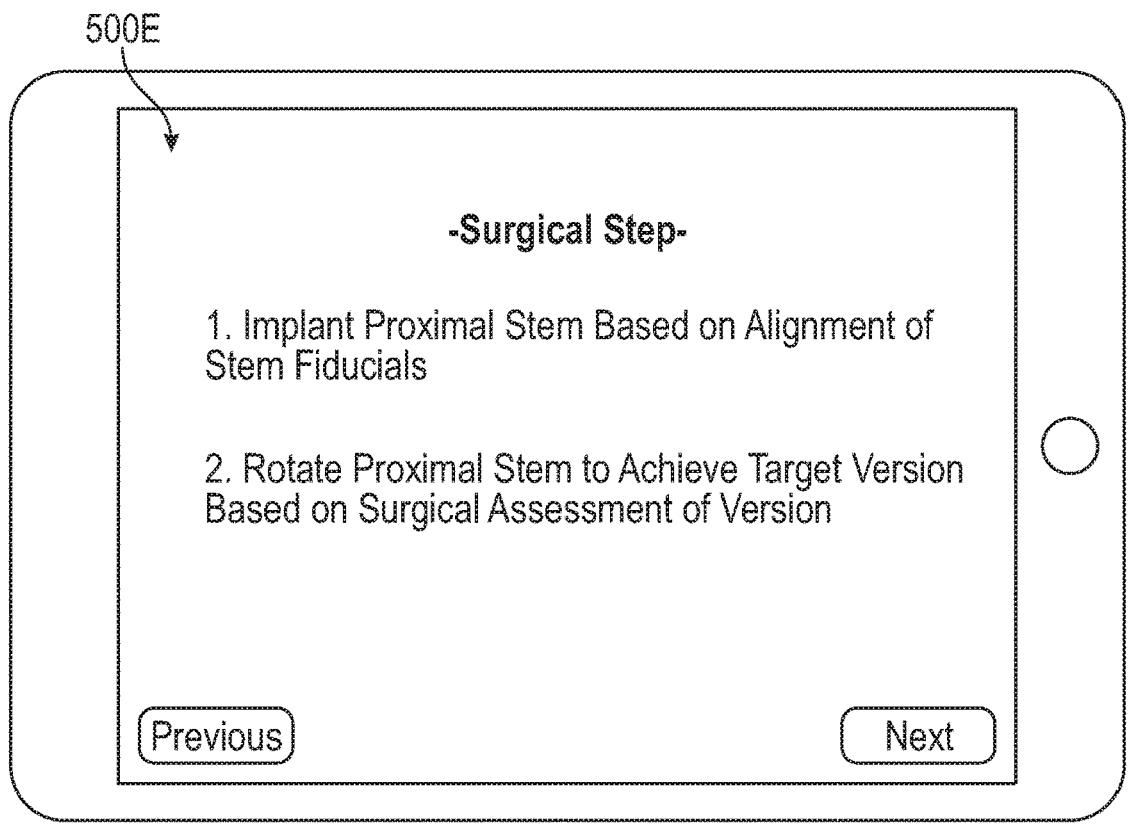
Figure 5F:
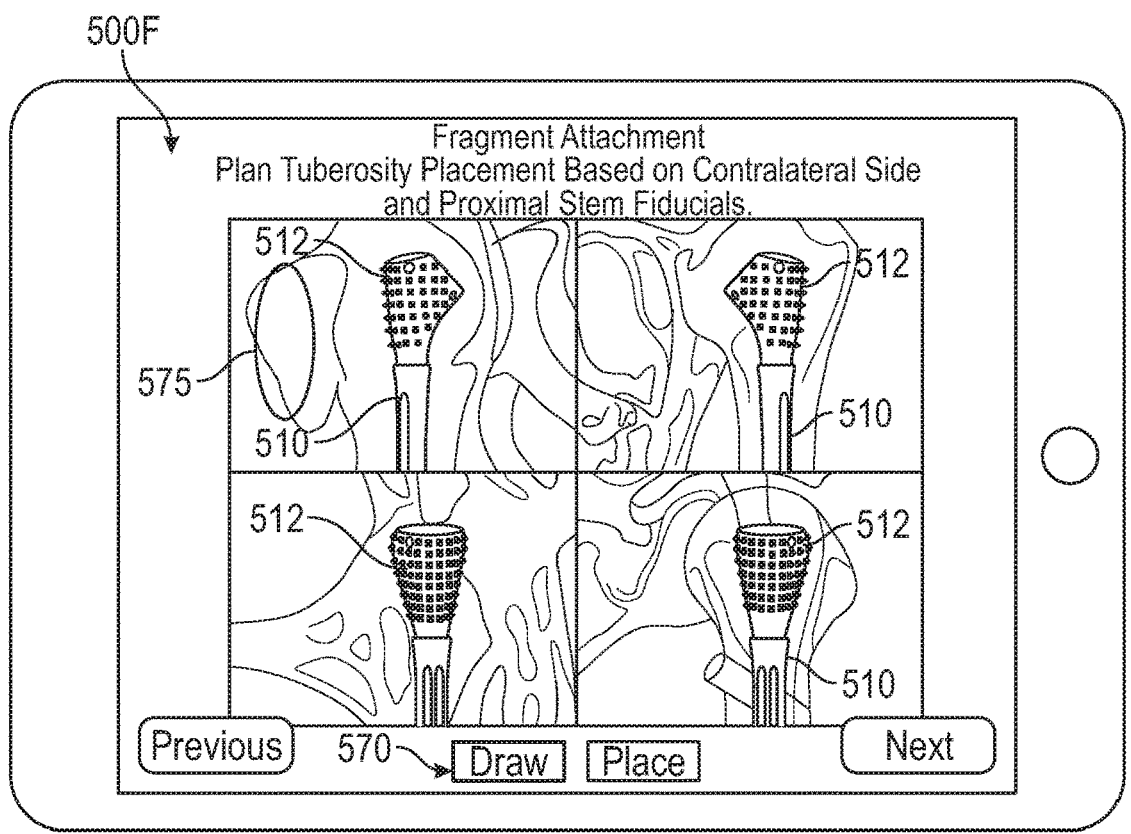

FIG. 5E depicts an interface 500E with instructions for a surgical operation; in this example the surgical operation is implanting of the proximal stem and adjusting the version. FIG. 5F depicts an interface 500F, which in this example is a bone fragment placement planning interface. The interface 500F includes distal stem 510, proximal stem 512, fragment identification control 570, and fragment identification tool 575. The interface 500F overlays information on four different images, AP and ML images of the target joint as well as AP and ML images of the contralateral joint. The fragments will be worked on within the target joint images, with the contralateral joint shown to assist the surgeon with placement. Fragment identification can be done with the fragment identification tool 575, which in this example involves drawing outlines around the bone fragments in the images. The intraoperative planning system 200 allows the surgeon to move and rotate the bone fragments to position them in desired locations around the implants.

Figure 6:
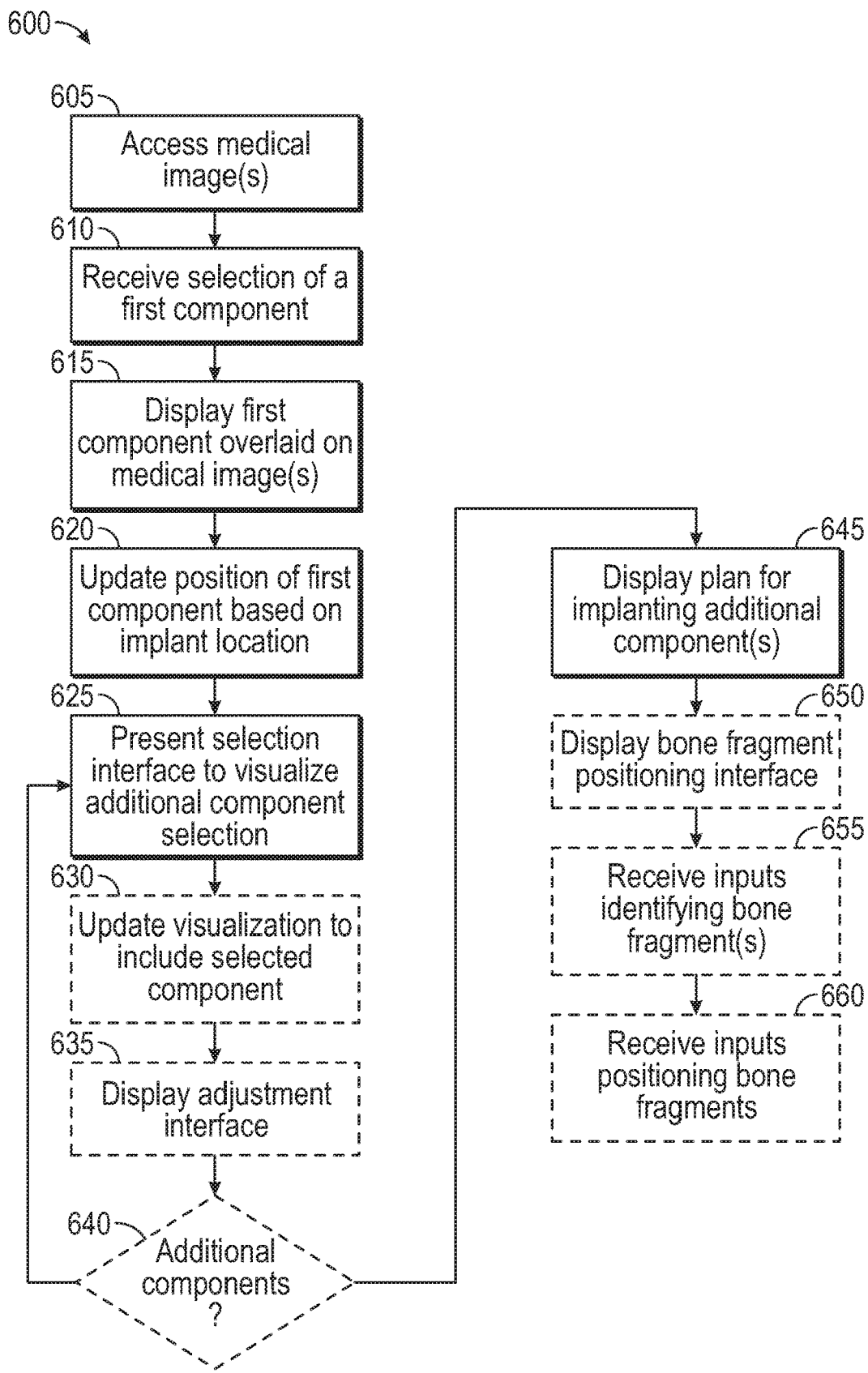
FIG. 6 is a flowchart illustrating a planning procedure, according to some example embodiments.

FIG. 6 is a flowchart illustration a planning procedure 600, according to some example embodiments. In this example, the planning procedure 600 includes operations such as accessing medical image(s) at 605, receiving selection of a first component at 610, displaying the first component overlaid on medical image(s) at 615, updating position of first component based on implant location at 620, presenting selection interface at 625, optionally updating visualization at 630, optionally displaying adjustment interface at 635, optionally determining if additional components are to be planned at 640, displaying plan for implanting additional components at 645, optionally displaying bone fragment interface at 650, optionally receiving inputs identifying bone fragments at 655, and optionally receiving input positioning bone fragments at 660.

At 605, the planning procedure 600 begins with the intraoperative planning system 200 accessing medical images (one or more) associated with the target joint under repair or reconstruction. The intraoperative planning system 200 can have the medical images stored locally or access them over a network on a medical image database, such as medical image database 240. At 610, the planning procedure 600 continues with the intraoperative planning system 200 receiving selection of a first component through a user-interface, such as those discussed above in reference to FIGS. 5A-5F. The selection of the first component corresponds to the first component of a modular prosthesis system to be used in the joint repair or reconstruction. In some examples, the selection of the first component will correspond to a first component already implanted in the patient. In other examples, the surgeon uses the intraoperative planning system 200 to confirm size and ideal implant location. For example, in the shoulder example discussed above, the surgeon can use the intraoperative planning system 200 to visualize distal stem size and seating depth within a patient's humerus prior to performing the implant surgery.

At 615, the planning procedure 600 continues with the intraoperative planning system 200 displaying the first component overlaid on the medical images within a planning interface. As indicated above, the surgeon can manipulate position of the first component relative to the medical images, which are scaled to properly represent the selected first component in reference to the patient's anatomy. At 620, the planning procedure 600 continues with the intraoperative planning system 200 updating position of the virtual first component based on inputs indicating the actual position of the implanted first component. Enabling the surgeon to adjust the planning procedure 600 based on intraoperative results allows for greater accuracy in placement and visualization of additional components of a modular prosthesis system.

At 620, the planning procedure 600 continues with the intraoperative planning system 200 presenting a selection interface to visualize selection and positioning of an additional component of a modular prosthesis system, such as a proximal stem in the modular should prosthesis. At 630, the planning procedure 600 optionally continues with the intraoperative planning system 200 updating the planning interface visualizations with the selected additional component. The planning procedure 600 optionally continues with the intraoperative planning system 200 displaying an adjustment interface for the additional component, allowing positional movement or rotational adjustments. At 640, the planning procedure 600 loops back to add additional components if the modular prosthesis system includes additional components for size and position planning. For example, in the discussed shoulder reconstruction, the head of the prosthesis system would still need to be selected and positioned.

At 645, after all components have been planned, the planning procedure 600 can continue with the intraoperative planning system 200 displaying an implant plan for implanting the additional components. In some examples, the intraoperative planning system 200 displays the implant plan after each additional component is added to facilitate iterative implant and planning for each additional component.

Optionally, at 650, the planning procedure 600 continues with the intraoperative planning system displaying a bone fragment planning interface that enables identification and positioning of bone fragments. At 655, the planning procedure 600 continues with the intraoperative planning system 200 receiving inputs identifying bone fragments. Inputs identifying bone fragments can include touch inputs over individual bone fragments, or drawing outlines around groups of bone fragments. Once the bone fragments are identified, the planning procedure 600 can continue at 660 with the intraoperative planning system 200 receiving inputs positioning bone fragments within an interface display multiple medical image from different angles to assist in positioning. The surgeon can then use the visualizations provided by the intraoperative planning system 200 to implement the bone fragment repair plan.

Software Architecture

Figure 7:
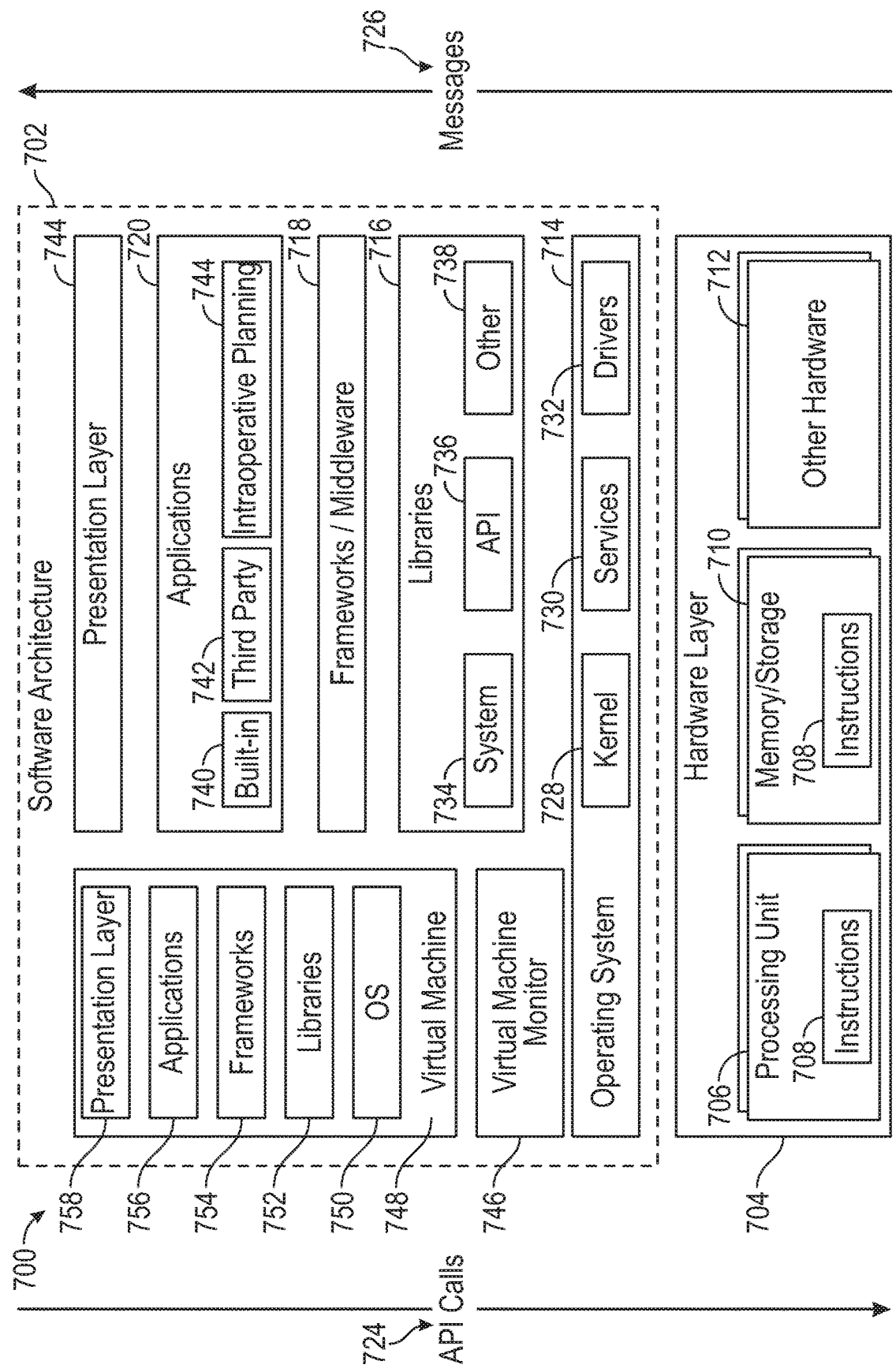
FIG. 7 is a block diagram illustrating an example of a software architecture that may be installed on a machine, according to some example embodiments.

FIG. 7 is a block diagram 700 illustrating a representative software architecture 702, which may be used in conjunction with various hardware architectures herein described. FIG. 7 is merely a non-limiting example of a software architecture and it will be appreciated that many other architectures may be implemented to facilitate the functionality described herein. The software architecture 702 may be executing on hardware such as machine 800 of FIG. 8 that includes, among other things, processors 810, memory 830, and I/O components 850. A representative hardware layer 704 is illustrated and can represent, for example, the machine 800 of FIG. 8. The representative hardware layer 704 comprises one or more processing units 706 having associated executable instructions 708. Executable instructions 708 represent the executable instructions of the software architecture 702, including implementation of the methods, modules and so forth of FIGS. 4-6. Hardware layer 704 also includes memory and/or storage modules 710, which also have executable instructions 708. Hardware layer 704 may also comprise other hardware as indicated by 78 which represents any other hardware of the hardware layer 704, such as the other hardware illustrated as part of machine 800.

In the example architecture of FIG. 7, the software 702 may be conceptualized as a stack of layers where each layer provides particular functionality. For example, the software 702 may include layers such as an operating system 714, libraries 716, frameworks/middleware 718, applications 720 and presentation layer 722. Operationally, the applications 720 and/or other components within the layers may invoke application programming interface (API) calls 724 through the software stack and receive a response, returned values, and so forth illustrated as messages 726 in response to the API calls 724. The layers illustrated are representative in nature and not all software architectures have all layers. For example, some mobile or special purpose operating systems may not provide a frameworks/middleware layer 718, while others may provide such a layer. Other software architectures may include additional or different layers.

The operating system 714 may manage hardware resources and provide common services. The operating system 714 may include, for example, a kernel 728, services 730, and drivers 732. The kernel 728 may act as an abstraction layer between the hardware and the other software layers. For example, the kernel 728 may be responsible for memory management, processor management (e.g., scheduling), component management, networking, security settings, and so on. The services 730 may provide other common services for the other software layers. The drivers 732 may be responsible for controlling or interfacing with the underlying hardware. For instance, the drivers 732 may include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 716 may provide a common infrastructure that may be utilized by the applications 720 and/or other components and/or layers. The libraries 716 typically provide functionality that allows other software modules to perform tasks in an easier fashion than to interface directly with the underlying operating system 714 functionality (e.g., kernel 728, services 730 and/or drivers 732). The libraries 716 may include system 734 libraries (e.g., C standard library) that may provide functions such as memory allocation functions, string manipulation functions, mathematic functions, and the like. In addition, the libraries 716 may include API libraries 736 such as media libraries (e.g., libraries to support presentation and manipulation of various media format such as MPREG4, H.264, MP3, AAC, AMR, JPG, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 716 may also include a wide variety of other libraries 738 to provide many other APIs to the applications 720 and other software components/modules.

The frameworks 718 (also sometimes referred to as middleware) may provide a higher-level common infrastructure that may be utilized by the applications 720 and/or other software components/modules. For example, the frameworks 718 may provide various graphic user interface (GUI) functions, high-level resource management, high-level location services, and so forth. The frameworks 718 may provide a broad spectrum of other APIs that may be utilized by the applications 720 and/or other software components/modules, some of which may be specific to a particular operating system or platform.

The applications 720 include built-in applications 740, third party applications 742, or intraoperative planning applications 744. Examples of representative built-in applications 740 may include, but are not limited to, a contacts application, a browser application, a book reader application, a location application, a media application, a messaging application, and/or a game application. Third party applications 742 may include any of the built in applications as well as a broad assortment of other applications. In a specific example, the third party application 742 (e.g., an application developed using the Android™ or iOS™ software development kit (SDK) by an entity other than the vendor of the particular platform) may be mobile software running on a mobile operating system such as iOS™, Android™, Windows® Phone, or other mobile operating systems. In this example, the third party application 742 may invoke the API calls 724 provided by the mobile operating system such as operating system 714 to facilitate functionality described herein. The intraoperative planning application(s) 744 can include programming logic to implement the methods and user interfaces discussed above providing intraoperative planning capabilities discussed herein. The intraoperative planning application(s) 744 function to improve the operation of the computing device for use by surgeon or related medical personnel within an orthopedic surgical environment. In this example, without the intraoperative planning application(s) 744 the computing device would be unable to perform any of the functions discussed in reference to FIGS. 4-6.

The applications 720 may utilize built in operating system functions (e.g., kernel 728, services 730 and/or drivers 732), libraries (e.g., system 734, APIs 736, and other libraries 738), frameworks/middleware 718 to create user interfaces to interact with users of the system. Alternatively, or additionally, in some systems interactions with a user may occur through a presentation layer, such as presentation layer 744. In these systems, the application/module "logic" can be separated from the aspects of the application/module that interact with a user.

Some software architectures utilize virtual machines. In the example of FIG. 7, this is illustrated by virtual machine 748. A virtual machine creates a software environment where applications/modules can execute as if they were executing on a hardware machine (such as the machine of FIG. 8, for example). A virtual machine is hosted by a host operating system (operating system 714 in FIG. 8) and typically, although not always, has a virtual machine monitor 746, which manages the operation of the virtual machine as well as the interface with the host operating system (i.e., operating system 714). A software architecture executes within the virtual machine such as an operating system 750, libraries 752, frameworks/middleware 754, applications 756 and/or presentation layer 758. These layers of software architecture executing within the virtual machine 748 can be the same as corresponding layers previously described or may be different.

Example Machine Architecture and Machine-Readable Medium

Figure 8:
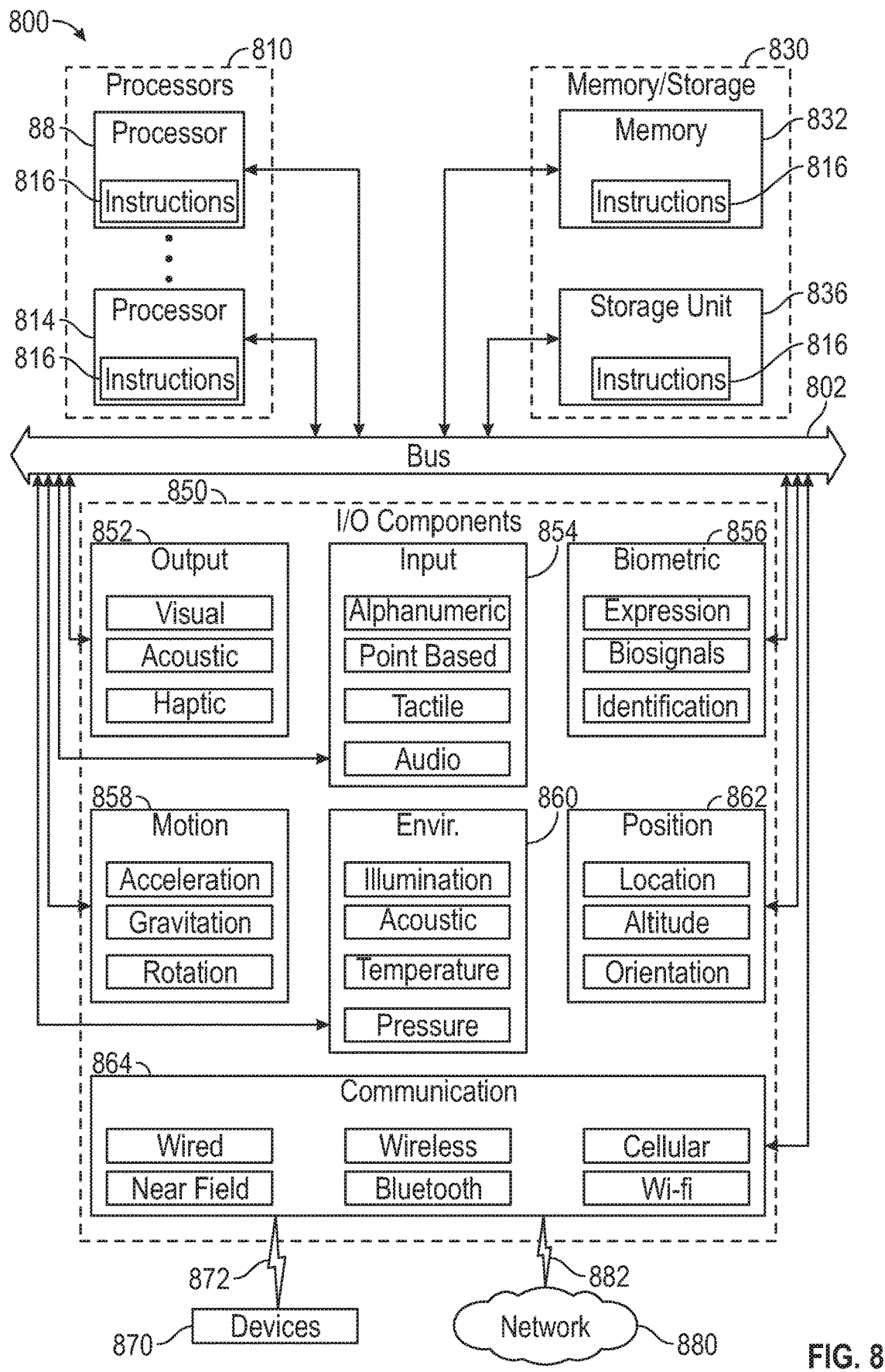
FIG. 8 illustrates a diagrammatic representation of a machine in the form of a computer system within which a set of instructions may be executed for causing the machine to perform any one or more of the methodologies discussed herein, according to an example embodiment.

FIG. 8 is a block diagram illustrating components of a machine 800, according to some example embodiments, able to read instructions from a machine-readable medium (e.g., a machine-readable storage medium) and perform any one or more of the methodologies discussed herein. Specifically, FIG. 8 shows a diagrammatic representation of the machine 800 in the example form of a computer system, within which instructions 816 (e.g., software, a program, an application, an applet, an app, or other executable code) for causing the machine 800 to perform any one or more of the methodologies discussed herein may be executed. For example the instructions may cause the machine to execute the flow diagrams of FIGS. 4 and 6. Additionally, or alternatively, the instructions may implement modules 222-226 of FIG. 2, and so forth. Further, the instruction may generate the planning interfaces illustrated in FIGS. 5A-5F. The instructions transform the general, non-programmed machine into a particular machine programmed to carry out the described and illustrated functions in the manner described. In alternative embodiments, the machine 800 operates as a standalone device or may be coupled (e.g., networked) to other machines. In a networked deployment, the machine 800 may operate in the capacity of a server machine or a client machine in a server-client network environment, or as a peer machine in a peer-to-peer (or distributed) network environment. The machine 800 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), or any machine capable of executing the instructions 816, sequentially or otherwise, that specify actions to be taken by machine 800. Further, while only a single machine 800 is illustrated, the term "machine" shall also be taken to include a collection of machines 800 that individually or jointly execute the instructions 816 to perform any one or more of the methodologies discussed herein.

The machine 800 may include processors 810, memory 830, and I/O components 850, which may be configured to communicate with each other such as via a bus 802. In an example embodiment, the processors 810 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, processor 88 and processor 814 that may execute instructions 816. The term "processor" is intended to include multi-core processor that may comprise two or more independent processors (sometimes referred to as "cores") that may execute instructions contemporaneously. Although FIG. 8 shows multiple processors, the machine 800 may include a single processor with a single core, a single processor with multiple cores (e.g., a multi-core process), multiple processors with a single core, multiple processors with multiples cores, or any combination thereof.

The memory/storage 830 may include a memory 832, such as a main memory, or other memory storage, and a storage unit 836, both accessible to the processors 810 such as via the bus 802. The storage unit 836 and memory 832 store the instructions 816 embodying any one or more of the methodologies or functions described herein. The instructions 816 may also reside, completely or partially, within the memory 832, within the storage unit 836, within at least one of the processors 810 (e.g., within the processor's cache memory), or any suitable combination thereof, during execution thereof by the machine 800. Accordingly, the memory 832, the storage unit 836, and the memory of processors 810 are examples of machine-readable media.

As used herein, "machine-readable medium" means a device able to store instructions and data temporarily or permanently and may include, but is not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 816. The term "machine-readable medium" shall also be taken to include any medium, or combination of multiple media, that is capable of storing instructions (e.g., instructions 816) for execution by a machine (e.g., machine 800), such that the instructions, when executed by one or more processors of the machine 800 (e.g., processors 810), cause the machine 800 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 850 may include a wide variety of components to receive input, provide output, produce output, transmit information, exchange information, capture measurements, and so on. The specific I/O components 850 that are included in a particular machine will depend on the type of machine. For example, portable machines such as mobile phones will likely include a touch input device or other such input mechanisms, while a headless server machine will likely not include such a touch input device. It will be appreciated that the I/O components 850 may include many other components that are not shown in FIG. 8. The I/O components 850 are grouped according to functionality merely for simplifying the following discussion and the grouping is in no way limiting. In various example embodiments, the I/O components 850 may include output components 852 and input components 854. The output components 852 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 854 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 850 may include biometric components 856, motion components 858, environmental components 860, or position components 862 among a wide array of other components. For example, the biometric components 856 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 858 may include acceleration sensor components (e.g., accelerometer), gravitation sensor components, rotation sensor components (e.g., gyroscope), and so forth. The environmental components 860 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 862 may include location sensor components (e.g., a Global Position System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 850 may include communication components 864 operable to couple the machine 800 to a network 880 or devices 870 via coupling 882 and coupling 872 respectively. For example, the communication components 864 may include a network interface component or other suitable device to interface with the network 880. In further examples, communication components 864 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 870 may be another machine or any of a wide variety of peripheral devices (e.g., a peripheral device coupled via a Universal Serial Bus (USB)).

Moreover, the communication components 864 may detect identifiers or include components operable to detect identifiers. For example, the communication components 864 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 864, such as, location via Internet Protocol (IP) geo-location, location via Wi-Fi® signal triangulation, location via detecting a NFC beacon signal that may indicate a particular location, and so forth.

Transmission Medium

In various example embodiments, one or more portions of the network 880 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network 880 or a portion of the network 880 may include a wireless or cellular network and the coupling 882 may be a Code Division Multiple Access (CDMA) connection, a Global System for Mobile communications (GSM) connection, or other type of cellular or wireless coupling. In this example, the coupling 882 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The instructions 816 may be transmitted or received over the network 880 using a transmission medium via a network interface device (e.g., a network interface component included in the communication components 864) and utilizing any one of a number of well-known transfer protocols (e.g., hypertext transfer protocol (HTTP)). Similarly, the instructions 816 may be transmitted or received using a transmission medium via the coupling 872 (e.g., a peer-to-peer coupling) to devices 870. The term "transmission medium" shall be taken to include any intangible medium that is capable of storing, encoding, or carrying instructions 816 for execution by the machine 800, and includes digital or analog communications signals or other intangible medium to facilitate communication of such software.

Language

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled. As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

Various Notes & Examples

Each of the following non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

Examples

Example 1 describes an intraoperative surgical planning technique operating on a computing device available within the operating room. The technique in this example can being by accessing, on a computing device operating an intraoperative surgical planning interface, a first medical image providing a first view of a joint within a surgical site. The technique can continue by receiving, within the intraoperative surgical planning interface, selection of a first component of a modular prosthetic device implanted in the first bone of the joint. The technique further includes operations to display, within the intraoperative surgical planning interface, a graphical representation of the first component of the modular prosthetic device overlaid on the first medical image. The described technique also includes updating the graphical representation of the first component based on receiving, within the intraoperative surgical planning interface, positioning inputs representative of an implant location of the first component relative to landmarks on the first bone visible within the first medical image. In this example, the technique concludes by presenting, within the intraoperative surgical planning interface, a selection interface enabling visualization of additional components of the modular prosthetic device virtually connected to the first component and overlaid on the first medical image.

In example 2, the subject matter of example 1 can optionally include the first component implanted within the first bone including a plurality of fiducial marks indicative of position, and the technique further including receiving the positioning inputs includes receiving indication of relationship between at least one fiducial mark of the plurality of fiducial marks on the first component and the first bone.

In example 3, the subject matter of any one of examples 1 and 2 can optionally include displaying the graphical representation of the first component by displaying fiducial marks on the first component within the intraoperative surgical planning interface corresponding to fiducial marks on the implanted first component to assist in correlating between the intraoperative surgical planning interface and the surgical site.

In example 4, the subject matter of any one of examples 1 to 3 can optionally include subsequent to receiving selection of a second component via the selection interface, the technique can include updating the graphical representation to include the first component coupled to the second component of the modular prosthetic device.

In example 5, the subject matter of example 4 can optionally include presenting, within the intraoperative surgical planning interface, an adjustment interface enabling adjustment of the second component relative to the first component, wherein the adjustments available within the intraoperative surgical planning interface are constrained by available physical adjustments between the first component and the second component of the modular prosthetic device.

In example 6, the subject matter of example 5 can optionally include available physical adjustments such as height adjustment along a longitudinal axis and rotational adjustment relative to the longitudinal axis.

In example 7, the subject matter of any one of examples 5 and 6 can optionally include presenting the adjustment interface by displaying fiducial marks on the first component and the second component that correspond to physical fiducial marks on the first component and the second component to enable translation of adjustments performed within the adjustment interface to the modular prosthetic device implanted within the joint.

In example 8, the subject matter of any one of examples 5 to 7 can optionally include accessing the first medical image along with accessing a second medical image providing a second view of a contralateral joint, wherein presenting the adjustment includes presenting a second graphical representation of the modular prosthetic device overlaid on the second medical image.

In example 9, the subject matter of any one of examples 1 to 8 can optionally include accessing the first medical image along with accessing a second medical image providing a second view of a contralateral joint, wherein the presenting the selection interface includes presenting a second graphical representation of modular prosthetic device overlaid on the second medical image.

In example 10, the subject matter of any one of examples 1 to 9 can optionally include the technique further comprising presenting, within the intraoperative surgical planning interface, a bone fragment positioning interface enabling identification and positioning of bone fragments within the first medical image relative to the modular prosthetic device.

In example 11, the subject matter of example 10 can optionally include presenting the bone fragment positioning interface by receiving bone fragment identification inputs, via the bone fragment positioning interface, identifying a first bone fragment.

In example 12, the subject matter of example 11 can optionally include presenting the bone fragment positioning interface by receiving positioning inputs, via the bone frag-ment positioning interface, positioning the first bone fragment relative to the modular prosthetic device.

Example 13 describes a computer-assisted shoulder reconstruction surgical method that can be used within an operating room during a reconstruction procedure. The method can include implanting a distal stem of a modular shoulder prosthesis into a humerus to a depth providing good fixation, the distal stem including fiducial marks along at least a portion of the longitudinal length. In this example, the method can continue by accessing, from a computing device running a surgical planning application, a plurality of medical images of a shoulder joint involved in the shoulder reconstruction, the plurality of medical images including a first medical image depicting a first view including the shoulder joint and a second medical image depicting a second view including a contralateral shoulder joint. The method can also include selecting, within the surgical planning application, a virtual distal stem corresponding to the distal stem implanted into the humerus. The method can continue by adjusting, within the surgical planning application, a position of the virtual distal stem in reference to representations of the humerus in the first medical image and the second medical image using a comparison between the fiducial marks on the stem and corresponding virtual fiducial marks on the virtual distal stem. The method can further include selecting a proximal stem and further modular components based on interactive visualizations provided within the surgical planning application, the interactive visualizations presented in reference to the virtual distal stem within the first medical image and the second medical image. In this example, the method can conclude by implanting the proximal stem and further modular components selected based on the interactive visualizations provided by the surgical planning application. In another example, the method discussed here can conclude with an implantation plan for implanting the proximal stem and further modular components selected based on the interactive visualizations provided by the surgical planning application can be output for use by a surgeon.

In example 14, the subject matter of example 13 can optionally include selecting the proximal stem by manipulating a position of a virtual proximal stem with respect to the virtual distal stem visualized within the first medical image and the second medical image within the interactive visualizations provided by the surgical planning application.

In example 15, the subject matter of example 14 can optionally include manipulating the position of the virtual proximal stem with respect to the virtual distal stem is constrained by physical limitations in coupling the proximal stem with the distal stem.

In example 16, the subject matter of example 15, can optionally include manipulating position of the virtual proximal stem by adjusting a telescopic height along the longitudinal axis of the modular shoulder prosthesis to adjust head height.

In example 17, the subject matter of any one of examples 14 to 16 can optionally include manipulating position of the virtual proximal stem with respect to the virtual distal stem by adjusting rotation of the virtual proximal stem within a second interactive visualization interface including a third medical image and a fourth medical image, wherein the third medical image depicts a first axial view of the humerus and the fourth medical image depicts a second axial view of a contralateral humerus.

In example 18, the subject matter of example 18 can optionally include adjusting rotation of the virtual proximal stem by entering rotations in pre-defined degree increments relative to the distal stem to set version of the modular shoulder prosthesis.

In example 19, the subject matter of any one of examples 17 and 18 can optionally include implanting the proximal stem by rotating the proximal stem in reference to the distal stem to match the rotation of the virtual proximal stem within the second interactive visualization interface.

In example 20, the subject matter of any one of examples 13 to 19 can optionally include implanting the proximal stem and the head including matching fiducial marks on a virtual proximal stem and a virtual head within the interactive visualization with fiducial marks on the proximal stem and head of the modular shoulder prosthesis.

In example 21, the subject matter of any one of examples 13 to 20 can optionally include identifying, within the surgical planning application using a fragment interface, a bone fragment to be reattached during the shoulder reconstruction.

In example 22, the subject matter of example 21 can optionally include identifying the bone fragment further includes manipulating position or rotation of the bone fragment relative to a virtual representation of the modular shoulder prosthesis.

In example 23, the subject matter of example 22 can optionally include manipulating position or rotation of the bone fragment by visualizing the bone fragment within the first medical image and the second medical image.

In example 24, the subject matter of example 23 can optionally include visualizing the bone fragment by depicting the position and orientation of the bone fragment within a third medical image and a fourth medical image, wherein the third medical image provides third view including the shoulder joint with the modular prosthesis overlaid and the fourth medical image provides a fourth view including the contralateral shoulder joint with the modular prosthesis overlaid.

In example 25, the subject matter of any one of examples 22 to 24 can optionally include attaching the bone fragment based on a visualization of a final placement of the bone fragment within the fragment interface provided within the surgical planning application.

Example 26 describes a modular shoulder prosthesis for use in conjunction with any one of examples 1 to 25. The modular shoulder prosthesis including a distal stem including fiducial marks along at least a portion of a longitudinal length. The prosthesis also including a proximal stem detachably couplable with the distal stem, the proximal stem including height indicating fiducial marks along at least a portion of a longitudinal length and rotation indicating fiducial marks around a circumference of a portion of the proximal stem. Finally, the prosthesis includes a head, or reverse tray, or other modular components, detachably couplable with the proximal stem.

In example 27, the prosthesis of example 26 can optionally include the distal stem having rotation indicating fiducial marks around a circumference of a proximal portion corresponding to the rotation indicating fiducial marks on the proximal stem.

Example 28 describes a shoulder reconstruction system for use in conjunction with any one of examples 1 to 25. The system including a plurality of distal stems each distal stem of the plurality of distal stems having a different diameter or length and including fiducial marks along at least a portion of a longitudinal length. The system also including a plurality of proximal stems each proximal stem detachably couplable with a distal stem of the plurality of distal stems, each proximal stem including height indicating fiducial marks along at least a portion of a longitudinal length and rotation indicating fiducial marks around a circumference of a portion of the proximal stem. The system further including a plurality of heads, trays, or other modular components detachably couplable with a proximal stem of the plurality of proximal stems.

The claimed invention includes:

1. A multi-component prosthesis system for reconstruction of a joint, the system comprising:
   a first component including a body extending from a proximal end to a distal end, the body including a first plurality of fiducial marks comprising fiducial marks along at least a portion of a longitudinal length between the proximal end and the distal end;
   a second component movably couplable with the first component, the second component including a second plurality of fiducial marks comprising height indicating fiducial marks along at least a portion of a longitudinal length and rotation indicating fiducial marks around a circumference of a portion of the second component; and
   a computer system including memory, a processor, and a display, the memory containing instructions that, when executed by the processor, cause the computer system to:
   display a virtual graphical representation of at least one of the first component and the second component overlaid on a medical image of the joint, the virtual graphical representation including virtual fiducial marks corresponding to at least a portion of the first plurality of fiducial marks or the second plurality of fiducial marks.

2. The system of claim 1, wherein the memory contains additional instructions that cause the computer system to update the virtual graphical representation based on receiving positioning inputs representative of a location of at least one of the first component and the second component relative to landmarks on a bone visible within the medical image.

3. The system of claim 2, wherein receiving the positioning inputs includes receiving indication of relationship between at least one fiducial mark of the fiducial marks on the first component and the bone displayed within the medical image.

4. The system of claim 1, wherein the memory contains additional instructions that cause the computer system to update the virtual graphical representation to include the first component coupled to the second component.

5. The system of claim 4, wherein the memory contains additional instructions that cause the computer system to present an adjustment interface enabling adjustment of the virtual representation of the first component relative to the second component, wherein the adjustments available within the intraoperative surgical planning interface are constrained by available physical adjustments between the first component and the second component of the system.

6. The modular shoulder prosthesis system of claim 5, wherein the available physical adjustments between the first component and the second component include:
   height adjustment along a longitudinal axis; and
   rotational adjustment relative to the longitudinal axis.

7. The system of claim 5, wherein presenting the adjustment interface includes displaying fiducial marks on the virtual representation of the first component and the second component that correspond to physical fiducial marks on the first component and the second component to enable translation of adjustments performed within the adjustment interface to implanted and coupled first component and second component.

8. The system of claim 7, wherein the first plurality of fiducial marks includes rotational fiducial marks distributed around a periphery of the proximal end; and
wherein the rotation indicating fiducial marks on the second component correspond to the rotational fiducial marks distributed around the periphery of the proximal end of the first component.

9. The modular shoulder prosthesis system of claim 4, wherein the memory contains additional instructions that cause the computer system to:
access a second medical image providing a second view of a contralateral joint; and
wherein displaying the virtual graphical representation includes presenting a second graphical representation of the first component and the second component overlaid on the second medical image.

10. The modular shoulder prosthesis system of claim 9, wherein the memory contains additional instructions that cause the computer system to present an adjustment interface including input controls to manipulate a position of the virtual representation of the first component with respect to the virtual representation of the second component visualized overlaid on the medical image or the second medical image.

11. The modular shoulder prosthesis system of claim 1, wherein the memory contains additional instructions that cause the computer system to present a bone fragment positioning interface enabling identification and virtual positioning of bone fragments within the medial image relative to at least one of the first component and the second component.

12. The modular shoulder prosthesis system of claim 11, wherein presenting the bone fragment positioning interface includes receiving bone fragment identification inputs, via the bone fragment positioning interface, identifying a first bone fragment.

13. The modular shoulder prosthesis system of claim 12, wherein presenting the bone fragment positioning interface includes receiving positioning inputs, via the bone fragment positioning interface, positioning the first bone fragment relative to at least one of the first component and the second component.

14. The modular shoulder prosthesis system of claim 13, wherein positioning the first bone fragment includes manipulating position or rotation of the bone fragment.

15. The modular shoulder prosthesis system of claim 14, wherein manipulating position or rotation of the bone fragment includes visualizing the bone fragment within the medical image and the second medical image.

16. A modular shoulder prosthesis system comprising:
a distal stem including fiducial marks along at least a portion of a longitudinal length;
a proximal stem detachably couplable with the distal stem, the proximal stem including height indicating fiducial marks along at least a portion of a longitudinal length and rotation indicating fiducial marks around a circumference of a portion of the proximal stem;
a head, or reverse tray, or other modular components, detachably couplable with the proximal stem; and
a computer system including memory, a processor, and a display, the memory containing instructions that, when executed by the processor, cause the computer system to:
display a virtual graphical representation of at least one of the distal stem and the proximal stem overlaid on a medical image of a joint, the virtual graphical representation including virtual fiducial marks corresponding at least a portion of the fiducial marks on the distal stem or the proximal stem.

17. The modular shoulder prosthesis system of claim 16, wherein the memory contains additional instructions that cause the computer system to update the virtual graphical representation based on receiving positioning inputs representative of a location of at least one of the distal stem and the proximal stem relative to landmarks on the joint within the medical image.

18. The modular shoulder prosthesis system of claim 17, wherein receiving the positioning inputs includes receiving indication of relationship between at least one fiducial mark of the fiducial marks on the distal stem and a bone of the joint displayed within the medical image.

19. The modular shoulder prosthesis system of claim 16, wherein the distal stem is coupled to the proximal stem;
wherein the memory contains additional instructions that cause the computer system to present an adjustment interface enabling adjustment of the virtual representation of the proximal stem relative to the distal stem, wherein the adjustments available within the intraoperative surgical planning interface are constrained by available physical adjustments between the distal stem and the proximal stem of the modular shoulder prosthesis; and
wherein the available physical adjustments between the distal stem and the proximal stem include:
height adjustment along a longitudinal axis; and
rotational adjustment relative to the longitudinal axis.

20. The modular shoulder prosthesis system of claim 19, wherein presenting the adjustment interface includes displaying fiducial marks on the virtual representation of the distal stem and the proximal stem that correspond to physical fiducial marks on the distal stem and the proximal stem to enable translation of adjustments performed within the adjustment interface to the coupled distal stem and proximal stem.

* * * * *